United States Patent
Fujisaki

(10) Patent No.: US 10,864,306 B2
(45) Date of Patent: Dec. 15, 2020

(54) NEGATIVE-PRESSURE WOUND THERAPY APPARATUS

(71) Applicant: Murata Manufacturing Co., Ltd., Kyoto (JP)

(72) Inventor: Masaaki Fujisaki, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 624 days.

(21) Appl. No.: 15/400,007

(22) Filed: Jan. 6, 2017

(65) Prior Publication Data

US 2017/0112975 A1 Apr. 27, 2017

Related U.S. Application Data

(63) Continuation of application No. PCT/JP2015/068284, filed on Jun. 25, 2015.

(30) Foreign Application Priority Data

Jul. 8, 2014 (JP) .................. 2014-140147

(51) Int. Cl.
*A61F 13/00* (2006.01)
*A61M 1/00* (2006.01)

(52) U.S. Cl.
CPC ..... *A61M 1/0031* (2013.01); *A61F 13/00004* (2013.01); *A61F 13/00068* (2013.01);
(Continued)

(58) Field of Classification Search
CPC ........ A61F 13/00004; A61F 13/00068; A61M 1/0001; A61M 1/0031; A61M 1/0058; A61M 1/0066; A61M 1/009
See application file for complete search history.

(56) References Cited

U.S. PATENT DOCUMENTS 8,366,692 B2 * 2/2013 Weston ............... A61M 1/0037
604/319
2008/0082059 A1 4/2008 Fink et al.
(Continued)

FOREIGN PATENT DOCUMENTS

JP 2008080137 A 4/2008
JP 2011-512202 A 4/2011
(Continued)

OTHER PUBLICATIONS

International Search Report issued in Application No. PCT/JP2015/068284 dated Sep. 15, 2015.
(Continued)

*Primary Examiner* — Kai H Weng
(74) *Attorney, Agent, or Firm* — Pearne & Gordon, LLP

(57) ABSTRACT

Provided is a negative-pressure wound therapy apparatus capable of causing negative pressure in a closed space defined by a wound dressing and a wound region with a sufficient suction flow rate as needed even with a miniaturized pump device. In atypical use that needs a high suction flow rate, because a pump device (30) with a high suction flow rate is attached to a wound dressing (10) and sucks gas from a closed space (904) defined by a wound region (903) and the wound dressing (10), even when a pump device (20) for typical use is miniaturized and the suction flow rate of the pump device (20) is reduced, a therapy apparatus (100) can achieve a suction flow rate sufficient for atypical use. Thus, the pressure value in the closed space (904) can decrease to a desired value more quickly.

13 Claims, 6 Drawing Sheets

(52) U.S. Cl.
CPC .......... *A61M 1/0001* (2013.01); *A61M 1/009* (2014.02); *A61M 1/0058* (2013.01); *A61M 1/0066* (2013.01)

(56) References Cited

U.S. PATENT DOCUMENTS

| | | | |
|---|---|---|---|
| 2009/0312723 A1* | 12/2009 | Blott | A61M 1/0058 604/290 |
| 2010/0042021 A1 | 2/2010 | Hu | |
| 2010/0106184 A1* | 4/2010 | Coward | A61M 1/0088 606/213 |
| 2012/0046625 A1 | 2/2012 | Johannison | |
| 2013/0131616 A1* | 5/2013 | Locke | A61M 1/0031 604/321 |
| 2016/0175497 A1 | 6/2016 | Fink | |

FOREIGN PATENT DOCUMENTS

| | | | |
|---|---|---|---|
| JP | 2012-090813 A | 5/2012 | |
| JP | 2012-525202 A | 10/2012 | |
| JP | 2013-255824 A | 12/2013 | |

OTHER PUBLICATIONS

Written Opinion issued in Application No. PCT/JP2015/068284 dated Sep. 15, 2015.

* cited by examiner

NEGATIVE-PRESSURE WOUND THERAPY APPARATUS

This is a continuation of International Application No. PCT/JP2015/068284 filed on Jun. 25, 2015 which claims priority from Japanese Patent Application No. 2014-140147 filed on Jul. 8, 2014. The contents of these applications are incorporated herein by reference in their entireties.

BACKGROUND OF THE DISCLOSURE

Field of the Disclosure

The present disclosure relates to a negative-pressure wound therapy apparatus for promoting a recovery in a wound region by application of negative pressure on a surface in the wound region.

Description of the Related Art

Negative-pressure wound therapy of promoting a recovery in a wound region by application of negative pressure on a surface in the wound region has been known in recent years. One example technique for the therapy is a negative-pressure wound therapy apparatus disclosed in Patent Document 1. The negative-pressure wound therapy apparatus includes a wound dressing for covering a wound region and a pump device for sucking gas from a closed space defined by the wound dressing and the wound region. The negative-pressure wound therapy apparatus described in Patent Document 1 causes negative pressure in the closed space by sucking gas from the closed space by using the pump device.

The pump device in the negative-pressure wound therapy apparatus described in Patent Document 1 also sucks an exudate exuding out from the surface in the wound region. The sucked exudate is stored in a storage portion (collection canister).

From the viewpoint of attachment to a user, small pump devices may be preferable in negative-pressure wound therapy apparatuses, including the pump device in the negative-pressure wound therapy apparatus described in Patent Document 1. If the pump device is small, the user can use the pump device while carrying it.

Patent Document 1: Japanese Unexamined Patent Application Publication No. 2013-255824

BRIEF SUMMARY OF THE DISCLOSURE

However, if the pump device is miniaturized, the pump for performing suction is also miniaturized, and the suction flow rate is reduced. Thus, if the pump device is miniaturized, the suction flow rate of the pump device may be insufficient when it is necessary to quickly cause negative pressure in the closed space.

Similarly, if the storage portion for storing an exudate is miniaturized, its storage capacity is reduced. Thus, if the storage portion is miniaturized, the storage capacity of the storage portion may be insufficient when it is necessary to store the exudate in large quantity.

Accordingly, it is an object of the present disclosure to provide a negative-pressure wound therapy apparatus capable of causing negative pressure in a closed space defined by a wound dressing and a wound region with a sufficient suction flow rate as needed even with a miniaturized pump device.

A negative-pressure wound therapy apparatus in the present disclosure includes a wound dressing that defines a closed space between a central portion in a principal surface thereof and a wound region by close contact of a peripheral portion in the principal surface with a periphery of a skin surface in the wound region, a first pump device including a first conduit attached to the wound dressing and a first inlet communicating with the closed space with the first conduit interposed therebetween, and a second pump device including a second conduit freely attachable to and detachable from the wound dressing and a second inlet communicating with the closed space with the second conduit interposed therebetween.

A suction flow rate of the second pump device is higher than a suction flow rate of the first pump device. The first pump device sucks fluid from the closed space through the first conduit and the first inlet. When the second conduit is attached to the wound dressing, the second pump device sucks fluid from the closed space through the second conduit and the second inlet.

Because the suction flow rate of the first pump device is lower than that of the second pump device, the pump for performing suction in the first pump device can be smaller than the pump in the second pump device. Accordingly, the first pump device can be smaller than the second pump device.

For example, in typical use by a user, the first pump device is driven to suck fluid from the closed space, whereas in atypical use by the user, the second pump device is driven to suck fluid from the closed space.

Typical use of the negative-pressure wound therapy apparatus indicates use when a flow rate of fluid sucked from the closed space (suction flow rate) can be low. For example, when the closed space has already been under sufficient negative pressure, a user detaches the second conduit from the wound dressing and uses the first pump device, which can be miniaturized, as typical use of the negative-pressure wound therapy apparatus. That is, in typical use of the negative-pressure wound therapy apparatus, the user detaches the second pump device from the wound dressing and uses only the first pump device. Atypical use of the negative-pressure wound therapy apparatus indicates use when a high suction flow rate is needed. For example, as atypical use, when the wound dressing has recently become attached to the wound region and it is necessary to quickly cause negative pressure in the closed space, the user attaches the second conduit to the wound dressing and uses the second pump device, which has a high suction flow rate.

The negative-pressure wound therapy apparatus according to the present disclosure can achieve a sufficient suction flow rate and cause negative pressure in the closed space as needed, even if the first pump device for typical use by the user is miniaturized, because in the case where a high suction flow rate is needed, the second pump device having the high suction flow rate is attached to the wound dressing and sucks fluid from the closed space defined by the wound region and wound dressing.

When the second conduit is attached to the wound dressing, the first pump device and the second pump device may be driven simultaneously.

Because that configuration can make the suction flow rate of the second pump device assist with that of the first pump device, the negative-pressure wound therapy apparatus can achieve a higher suction flow rate as needed.

The present disclosure is not limited to the configuration in which the suction flow rate of the second pump device is higher than that of the first pump device. Simply, when the second conduit is attached to the wound dressing, the first pump device and the second pump device may be driven simultaneously.

For example, even when the suction flow rate of the first pump device is equal to that of the second pump device, the user can use the second pump device in an auxiliary manner in atypical use.

The first pump device may include a first storage portion disposed in the first conduit. The second pump device may include a second storage portion disposed in the second conduit. A storage capacity of the second storage portion may be larger than a storage capacity of the first storage portion.

Because the second conduit is freely attachable to and detachable from the wound dressing, the second storage portion is freely attachable to and detachable from the wound dressing. With that configuration, the negative-pressure wound therapy apparatus can achieve a sufficient suction flow rate when necessary and can also achieve a sufficient storage capacity when required by storing an exudate from the wound region in the second storage portion.

The negative-pressure wound therapy apparatus may further include a cleaning tool including a third conduit attached to the wound dressing and a third storage portion, the third storage portion communicating with the closed space with the third conduit interposed therebetween and configured to store a cleaning solution for cleaning the wound region.

The cleaning solution cleans the wound region by continuously flowing from the third conduit through the closed space to the first conduit and the second conduit. In that configuration, because the second pump device is driven when a certain flow rate for the cleaning solution is needed, even if the first pump device is miniaturized, the wound region in the closed space can be cleaned by the cleaning solution with a sufficient flow rate.

To miniaturize the first pump device, it may have a configuration described above. For example, the first pump device may include a pump drivable by a piezoelectric element.

That is, the first pump device may preferably include the piezoelectric pump to have a small size. The piezoelectric pump may include a piezoelectric element and a diaphragm joined to the piezoelectric element. When an alternating voltage is applied to the piezoelectric element, it repeats expansion and contraction along the plane directions of the principal surface. When the piezoelectric element repeats expansion and contraction along the plane directions of the principal surface, it cause the joined diaphragm to bend and vibrate. The piezoelectric pump can be miniaturized more easily than an electromagnetic pump and the like. The piezoelectric pump is advantageous in that its vibration is weaker than that of the electromagnetic pump and the like. Moreover, when the frequency of the alternating voltage is 20 kHz or more, the sound of the vibration of the diaphragm is at or above 20 kHz, which is outside the audio-frequency range, and that sound is not easily perceptible by the user.

The negative-pressure wound therapy apparatus according to the present disclosure can achieve a sufficient suction flow rate and can cause negative pressure in the closed space as needed, even if the first pump device is miniaturized, because in the case where a certain suction flow rate is needed, the second pump device is attached to the wound dressing and sucks fluid from the closed space defined by the wound region and wound dressing.

DETAILED DESCRIPTION OF THE DISCLOSURE

Figure 1:
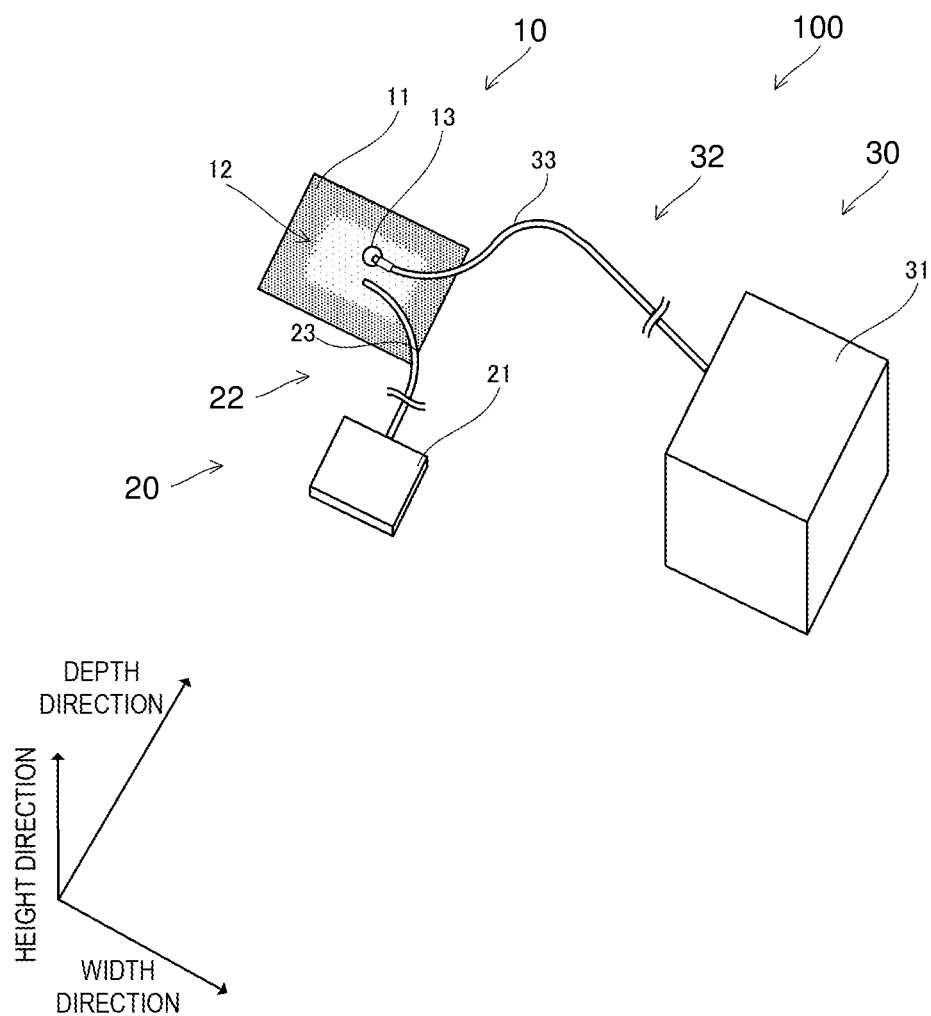
FIG. 1 is a perspective view from above of a therapy apparatus according to a first embodiment.
Figure 2:
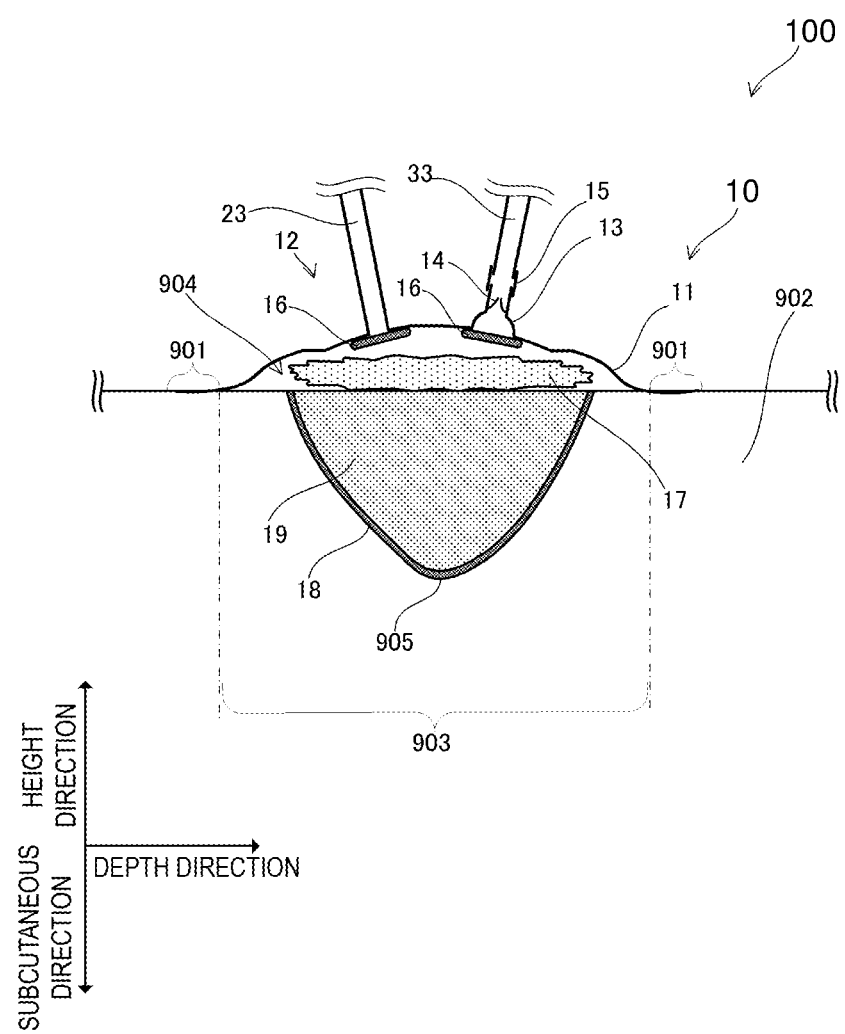
FIG. 2 is a side cross-sectional view of a wound dressing in the therapy apparatus according to the first embodiment when it is attached.

A therapy apparatus 100 according to a first embodiment is described with reference to FIGS. 1, 2, and 3. FIG. 2 illustrates in cross section a wound dressing 10 in the therapy apparatus 100 and an in vivo site 902, only the cross section of the wound dressing 10 is shown in gray, and the in vivo site 902 is not shown in gray. In FIGS. 1 and 2, a height direction is defined as upper side, and a direction opposite the height direction is defined as lower side.

The therapy apparatus 100 is used for negative-pressure wound therapy of promoting a recovery in a wound region by applying negative pressure on a surface in the wound region.

As illustrated in FIG. 1, the therapy apparatus 100 includes the wound dressing 10, a pump device 20 (corresponding to the first pump device), and a pump device 30 (corresponding to the second pump device).

As illustrated in FIG. 2, the wound dressing 10 includes a film 11, an absorbing member 17, a gauze 18, and a covering member 19.

The film 11 prevents the passage of liquid and gas. The absorbing member 17 absorbs liquid and holds the absorbed liquid. Examples of an element used as the absorbing member 17 may include cotton and gel in which a superabsorbent polymer is dispersed. The covering member 19 is a porous material that allows liquid to pass therethrough. An example of an element used as the covering member 19 may be a readily formable polyurethane foam.

In the attachment example illustrated in FIG. 2, in the plane directions of the wound dressing 10 (width direction and depth direction), the gauze 18 is in contact with a surface of a wound bed 905 inside a wound region indicated in a range 903 (hereinafter referred to as wound region 903). After the covering member 19 is shaped in accordance with the form of the wound bed 905, it is arranged above the gauze 18 so as to fill in the wound bed 905. The absorbing member 17 is arranged above the covering member 19. The film 11 is arranged so as to cover the absorbing member 17 and wound region 903 from above. Specifically, when the wound dressing 10 is seen in plan view, the peripheral portion in the lower surface of the film 11 is stuck on a skin surface 901 outside the wound region 903. Thus, the wound dressing 10 defines a closed space 904 between a central portion 12 (an area inside the peripheral portion) in the film 11 and the wound region 903.

As illustrated in FIG. 1, the pump device 20 in the pump device 20 includes a main body portion 21 and a conduit 22. The conduit 22 is described later.

Figure 3:
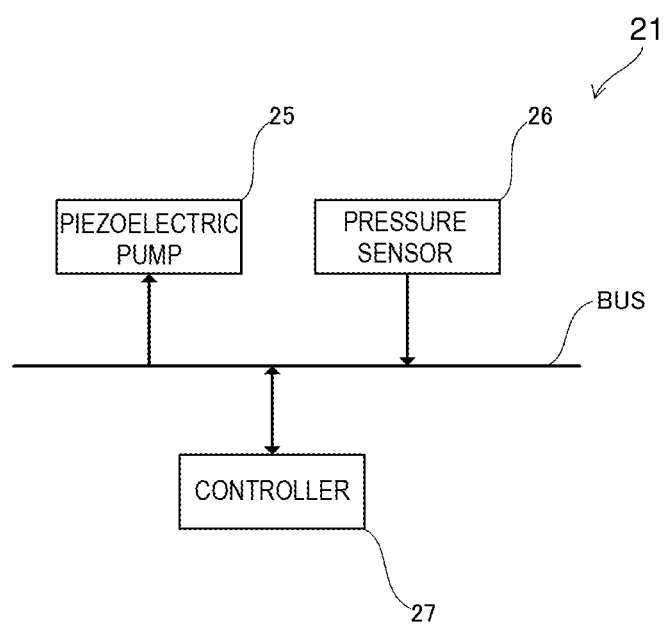
FIG. 3 is a block diagram that illustrates a part of a configuration of a main body portion in a first pump device in the therapy apparatus according to the first embodiment.

As illustrated in FIG. 3, the main body portion 21 includes a piezoelectric pump 25, a pressure sensor 26, and a controller 27. The piezoelectric pump 25, pressure sensor 26, and controller 27 are electrically connected to a shared bus. The piezoelectric pump 25, pressure sensor 26, and controller 27 are operated by power supplied from a battery included in the main body portion 21.

The piezoelectric pump 25 includes a diaphragm having a first principal surface and a second principal surface and a piezoelectric element disposed on at least one of the first principal surface and second principal surface of the diaphragm (none of these is illustrated). When an alternating voltage is applied to the piezoelectric element, the piezoelectric element repeats expansion and contraction in the directions of the principal surfaces. With the repetition of expansion and contraction of the piezoelectric element, the diaphragm bends and vibrates. The piezoelectric pump 25 transports gas from an inlet to an outlet by employing the bending and vibration of the diaphragm.

The piezoelectric pump 25 has a smaller size and lower profile than those of an electromagnetic pump, which employs electric currents and magnetic fields, or the like. Because the main body portion 21 in the pump device 20 includes the small and low-profile piezoelectric pump 25, it is small and thin to facilitate a user to carry it.

The vibration of the piezoelectric pump 25 is smaller than that of an electromagnetic pump or the like. When an alternating voltage applied to the piezoelectric element in the piezoelectric pump 25 has a frequency higher than the audio-frequency range (e.g., at or above 20 kHz), the sound of the vibration of the piezoelectric pump 25 is not easily perceptible by the user.

The pressure sensor 26 detects a pressure value at the inlet of the piezoelectric pump 25. The pressure sensor 26 outputs a detection signal corresponding to the detected pressure value to the controller 27. The controller 27 feedback-controls driving of the piezoelectric pump 25 such that the pressure value at the inlet of the piezoelectric pump 25 is in the range of 75 mmHg to 125 mmHg. The pressure sensor 26 may also detect a pressure value at any location other than the inlet of the piezoelectric pump 25 when the location is in a space communicating with the inlet.

Referring back to FIG. 1, the pump device 30 includes a main body portion 31 and a conduit 32. The main body portion 31 in the pump device 30 may include, for example, an electromagnetic pump (not illustrated). The electromagnetic pump is larger than the piezoelectric pump 25 in the pump device 20. Because the electromagnetic pump for performing suction in the pump device 30 is larger than the piezoelectric pump 25, the suction flow rate (ml/s) of the pump device 30 is higher than that of the pump device 20. The pump device 30 may include, for example, a plurality of piezoelectric pumps 25 driven in parallel, in place of the electromagnetic pump.

Next, the conduit 22 in the pump device 20 and the conduit 32 in the pump device 30 are described. Referring back to FIGS. 1 and 2, the conduit 22 extends from the closed space 904 to the inlet of the piezoelectric pump 25. A part of the conduit 22 is formed by attaching one end of a rubber tube 23 to the central portion 12 in the film 11 and attaching the other end to the main body portion 21.

The conduit 32 extends from the closed space 904 to the inlet of the electromagnetic pump in the main body portion 31. A part of the conduit 32 is formed by attaching one end of a rubber tube 33 to the central portion 12 in the film 11 and attaching the other end to the main body portion 31.

For the conduit 32, more specifically, the wound dressing 10 has a mounting port 13, as illustrated in FIG. 2. The mounting port 13 is disposed in the central portion 12 in the film 11. The mounting port 13 is equipped with a check valve 14 and a joint tube 15. The check valve 14 prevents fluid from flowing into the closed space 904. The joint tube 15 may have an internal diameter substantially the same as the external diameter of the rubber tube 33. One end of the rubber tube 33 is fit in the joint tube 15.

The conduit 32 in the pump device 30 is freely attachable to and detachable from the wound dressing 10 by insertion and removal of the rubber tube 33 into and from the joint tube 15. The conduit 32 may be attached to and detached from the wound dressing 10 by other methods without the use of the joint tube 15.

The therapy apparatus 100 includes two filters 16 prohibiting the passage of liquid and allowing only the passage of gas to prevent the liquid from flowing into the inlet of the piezoelectric pump 25 and the inlet of the electromagnetic pump in the pump device 30. In the example illustrated in FIG. 2, one of the filters 16 is arranged so as to cover the opening of the rubber tube 23 in the closed space 904, whereas the other filter 16 is arranged so as to cover the mounting port 13 in the closed space 904.

Next, the use of the therapy apparatus 100 is described with reference to FIGS. 4A and 4B. Here, typical use of the therapy apparatus 100 by a user 900 is defined as use when the flow rate for fluid sucked from the closed space 904 (hereinafter referred to as suction flow rate) can be low. For example, when the amount of an exudate from the surface of the wound bed 905 is small, the user 900 uses the therapy apparatus 100 in a typical manner. For example, when sufficient negative pressure has already been applied on the surface in the wound region 903, the user 900 uses the therapy apparatus 100 in a typical manner.

Atypical use of the therapy apparatus 100 by the user 900 is defined as use when a high suction flow rate is needed. For example, when the wound dressing 10 has recently become attached to the skin surface 901 and it is necessary to quickly cause negative pressure in the closed space 904, the user 900 uses the therapy apparatus 100 in an atypical manner. When the amount of an exudate from the surface of the wound bed 905 is large, the user 900 uses the therapy apparatus 100 in an atypical manner.

Figure 4A:
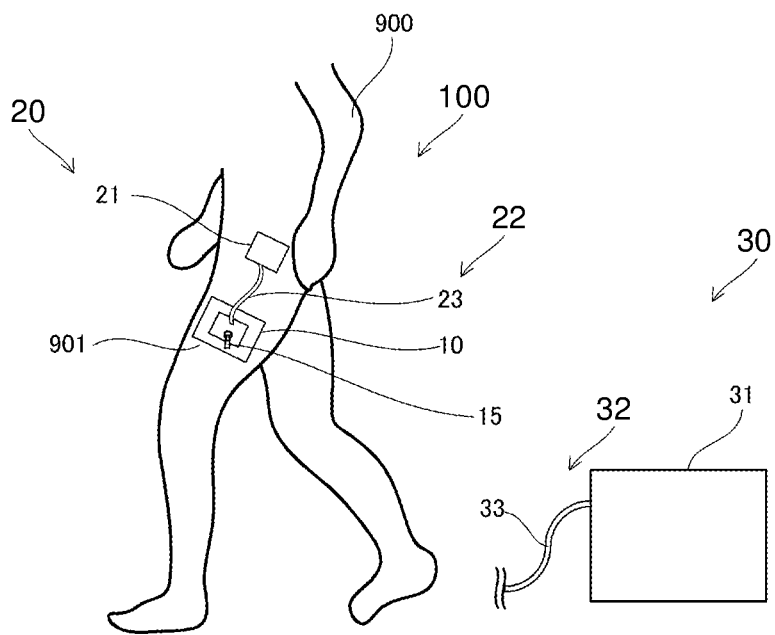
FIG. 4A is an illustration for describing typical use of the therapy apparatus according to the first embodiment.

As illustrated in FIG. 4A, in typical use of the therapy apparatus 100, the conduit 32 in the pump device 30 is detached from the wound dressing 10 by withdrawal of the rubber tube 33 from the joint tube 15. In typical use of the therapy apparatus 100, the pump device 20 sucks gas from the closed space 904 through the conduit 22 by driving the piezoelectric pump 25. Then, the pressure value in the closed space 904 gradually decreases.

Figure 4B:
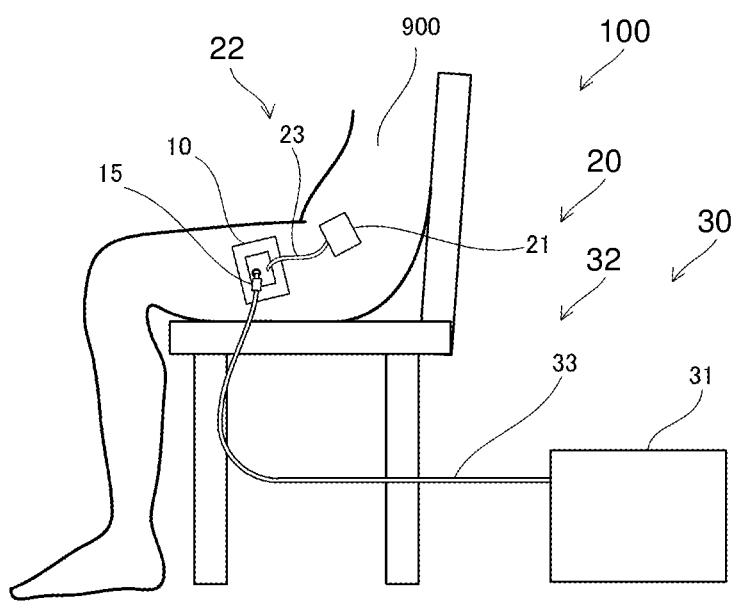
FIG. 4B is an illustration for describing atypical use of the therapy apparatus.

As illustrated in FIG. 4B, in atypical use of the therapy apparatus 100, the conduit 32 in the pump device 30 is attached to the wound dressing 10 by fitting of the rubber tube 33 in the joint tube 15. In atypical use of the therapy apparatus 100, the pump device 30 sucks gas from the closed space 904 through the conduit 32. Then, the pressure value in the closed space 904 gradually decreases.

The exudate from the wound bed 905 flows to the absorbing member 17 arranged on the negative-pressure side, and it is absorbed and held in the absorbing member 17.

As previously described, the suction flow rate of the pump device 30 is higher than that of the pump device 20. The amount of time elapsed to the time when a sufficient negative pressure is created in the closed space 904 (for example, a pressure value of 100 mmHg) depends on the suction flow rates of the pump device 20 and pump device 30. When the gas is sucked from the closed space 904 at a higher suction flow rate, the pressure value in the closed space 904 decreases more quickly.

In atypical use, at which a high suction flow rate is needed, the pump device 30 having a high suction flow rate is attached to the wound dressing 10 and sucks the gas from the closed space 904 defined by the wound region 903 and wound dressing 10. Thus, even when the pump device 20 for typical use is miniaturized and the suction flow rate of the pump device 20 is reduced, the therapy apparatus 100 according to the present embodiment can achieve a suction flow rate sufficient for atypical use. Accordingly, the pressure value in the closed space 904 decreases to a desired value more quickly.

In the therapy apparatus 100, the pump device 30 and pump device 20 may be driven simultaneously in atypical use. That is, the pump device 30 may be driven simultaneously with driving of the pump device 20 to assist with the suction flow rate of the pump device 20. This enables the pressure value in the closed space 904 to decrease to a desired value further quickly.

The therapy apparatus 100 may include two or more pump devices 30. In that case, the two or more pump devices 30 are individually driven in atypical use. The two or more pump devices 30 may be driven simultaneously with driving of the pump device 20 in atypical use.

In the above-described example, the suction flow rate of the pump device 30 driven in atypical use is higher than that of the pump device 20. If two or more pump devices are driven simultaneously in atypical use, the suction flow rate of the pump device driven only in atypical use may be equal to the suction flow rate of the pump device driven in typical use or may be lower than the suction flow rate of the pump device driven in typical use.

Figure 5:
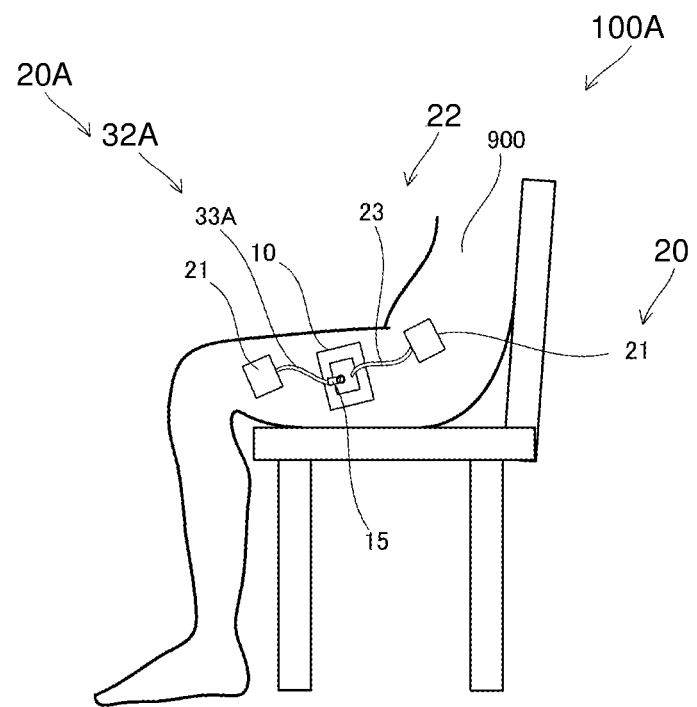
FIG. 5 is an illustration for describing atypical use of a therapy apparatus according to a variation of the therapy apparatus according to the first embodiment.

One example variation is illustrated in FIG. 5. A therapy apparatus 100A includes a pump device 20A, in place of the pump device 30. The configuration other than a conduit 32A in the pump device 20A is the same as that of the pump device 20. That is, the suction flow rate of the pump device 20A is equal to that of the pump device 20. The conduit 32A extends from the closed space 904 to the inlet of the piezoelectric pump 25 in the main body portion 21 in the pump device 20A. A part of the conduit 32A is formed from a rubber tube 33A. An end of the rubber tube 33A can be freely inserted in and removed from the joint tube 15.

In atypical use of the therapy apparatus 100A, the user 900 attaches the conduit 32A in the pump device 20A to the wound dressing 10 by fitting the end of the rubber tube 33A in the joint tube 15. The therapy apparatus 100A can achieve a suction flow rate sufficient for atypical use, even when the suction flow rate of the pump device 20A is equal to that of the pump device 20, because the suction flow rate of the pump device 20A assists with the suction flow rate of the pump device 20.

Next, a therapy apparatus 100B according to a second embodiment is described with reference to FIG. 6. In the above-described example, the absorbing member 17 for absorbing and holding an exudate from the surface of the wound bed 905 is arranged in the closed space 904. The therapy apparatus 100B according to the second embodiment includes a canister 28 (corresponding to the first storage portion) and a canister 34 (corresponding to the second storage portion) for storing the exudate. The canisters 28 and 34 are arranged outside the closed space 904. The description about the same configuration as that in the first embodiment is omitted.

Figure 6:
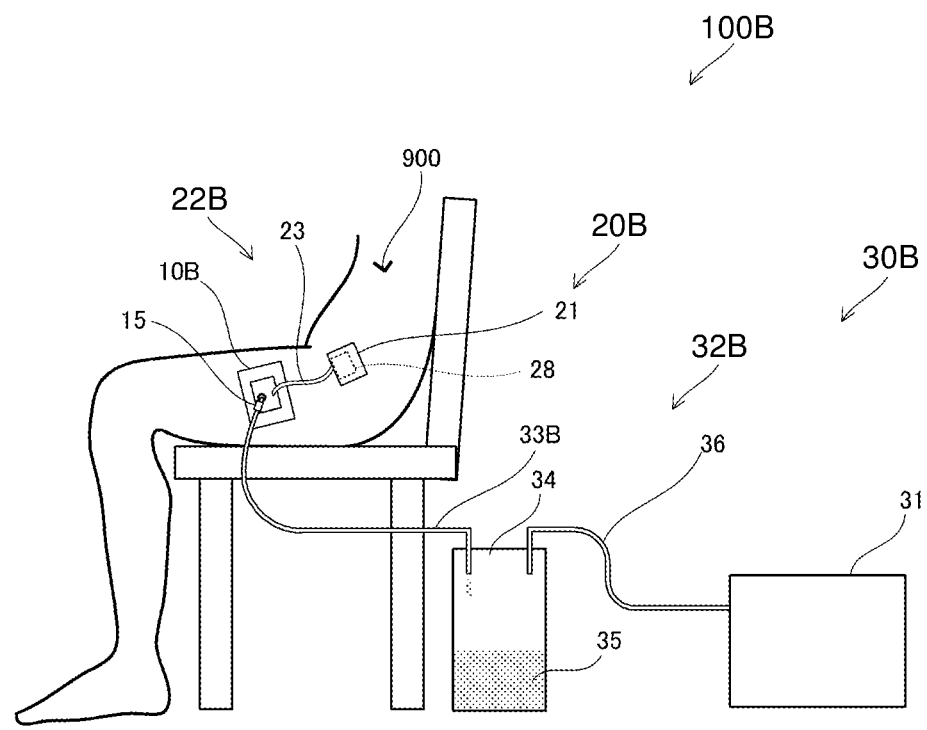
FIG. 6 is an illustration for describing atypical use of a therapy apparatus according to a second embodiment.

As illustrated in FIG. 6, specifically, the therapy apparatus 100B includes a wound dressing 10B, a pump device 20B, and a pump device 30B. In FIG. 6, only the canister 34 is illustrated in cross section to describe the storing of the exudate.

The wound dressing 10B differs from the wound dressing 10 according to the first embodiment in that the two filters 16 are omitted.

The pump device 20B includes the main body portion 21, a conduit 22B, and the canister 28. The conduit 22B differs from the conduit 22 according to the first embodiment in that the canister 28 is disposed in the conduit 22 and in that the conduit 22B allows the exudate to pass therethrough. In the example illustrated in FIG. 6, the canister 28 is arranged inside the main body portion 21. The canister 28 is a hermetic container for storing the exudate from the wound bed 905. When the piezoelectric pump 25 is driven, because the canister 28 is disposed in the conduit 22B, negative pressure is caused in the canister 28. Although not illustrated, the pump device 20B has a configuration for avoiding an exudate from flowing into the inlet of the piezoelectric pump 25 (for example, filter).

The pump device 30B includes the main body portion 31, a conduit 32B, and the canister 34. The conduit 32B differs from the conduit 32 according to the first embodiment in that its part is formed from a rubber tube 33B and a rubber tube 36, in that the canister 34 is disposed in the conduit 32B, and the conduit 32B allows the exudate to pass therethrough. In the example illustrated in FIG. 6, the canister 34 is arranged outside the main body portion 31. The canister 34 is a hermetic container for storing the exudate from the wound bed 905. The rubber tube 33B has a first end fit in the joint tube 15 and a second end inserted in the canister 34. The rubber tube 36 has a first end inserted in the canister 34 and a second end attached to the main body portion 31. The first end of the rubber tube 36 may be inserted in, for example, the upper portion in the canister 34 to prevent an exudate 35 transported to the canister 34 from flowing into the rubber tube 36.

The exudate storage capacity of the canister 34 is larger than the exudate storage volume of the canister 28.

Because the canister 34 is arranged outside the main body portion 31, it can be replaced merely by withdrawal of the rubber tube 33B and rubber tube 36 from the canister 34.

When the pump device 20B is driven and negative pressure is caused in the closed space 904, the exudate from the closed space 904 is transported to the canister 28 through a part of the conduit 22B. The canister 28 stores the transported exudate.

When the pump device 30B is driven and negative pressure is caused in the closed space 904, the exudate from the closed space 904 is transported to the canister 34 through the rubber tube 33B in the conduit 32B. The canister 34 stores the transported exudate 35.

In typical use of the therapy apparatus 100B, the pump device 30B is detached from the wound dressing 10B by withdrawal of the rubber tube 33B from the joint tube 15. In atypical use of the therapy apparatus 100B, the pump device 30B is attached to the wound dressing 10B by fitting of the rubber tube 33 in the joint tube 15. When the pump device 30B is attached to the wound dressing 10B, the canister 34 is also attached to the wound dressing 10B with the rubber tube 33B in the conduit 32B interposed therebetween.

The therapy apparatus 100B according to the present embodiment can cause negative pressure in the closed space 904 with a sufficient suction flow rate as needed. In addition, when it is necessary to store an exudate in large quantity, because the pump device 30B including the canister 34 having a large storage capacity is attached to the wound dressing 10B, even if the canister 28 is miniaturized and the storage capacity of the canister 28 is reduced, the therapy apparatus 100B can store the large quantity of the exudate as needed.

The storage capacity of the canister 34 may be equal to that of the canister 28 or may be smaller than that of the canister 28. In cases where the storage capacity of the canister 34 is equal to that of the canister 28 or is smaller than that of the canister 28, the pump devices 20B and pump device 30B are simultaneously driven and the exudate is simultaneously stored in the canisters 28 and 34.

Next, a therapy apparatus 100C according to a third embodiment is described with reference to FIGS. 7 and 8. The therapy apparatus 100C cleans the wound region 903 by using a cleaning solution tank 41.

The therapy apparatus 100C differs from the therapy apparatus 100B according to the second embodiment in that it includes a wound dressing 10C and a cleaning tool 40. The description about the same configuration as that in the therapy apparatus 100B is omitted.

Figure 7:
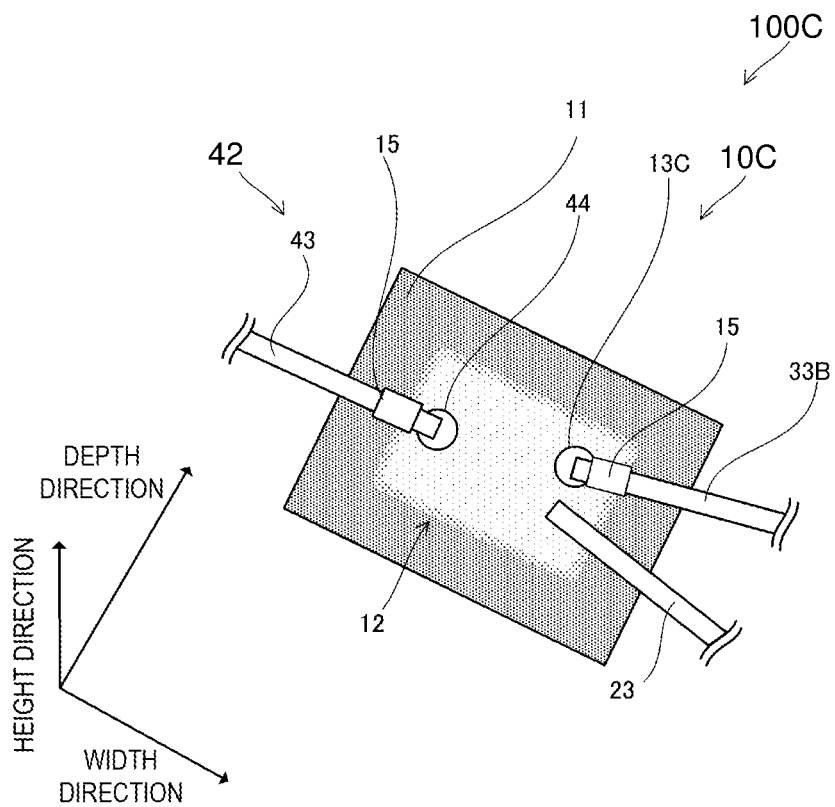
FIG. 7 is a perspective view from above of a wound dressing in a therapy apparatus according to a third embodiment.

As illustrated in FIG. 7, the wound dressing 10C differs from the wound dressing 10B according to the second embodiment in that it includes a mounting port 13C and a mounting port 44 in the central portion 12 and in that the rubber tube 23 is attached in a different location. The mounting port 13C differs from the mounting port 13 according to the third embodiment in that its arrangement is different. More specifically, the mounting port 13C is arranged in a location on an end portion side in the width direction in the central portion 12. The rubber tube 23 forming a part of the conduit 22B in the pump device 20B is attached to a location on the end portion side in the width direction in the central portion 12, as illustrated in FIG. 7. The mounting port 44 is arranged in a location on an end portion side in a direction opposite to the width direction in the central portion 12. The mounting port 44 is equipped with the joint tube 15.

The location of the mounting port 13C, the location of the mounting port 44, and the location where the rubber tube 23 is attached to the central portion 12 are not limited to the above-described examples. The mounting port 44 may preferably be spaced away from the location of the mounting port 13C and the location where the rubber tube 23 is attached in plane directions of the wound dressing 10C (the width direction and the depth direction).

Figure 8:
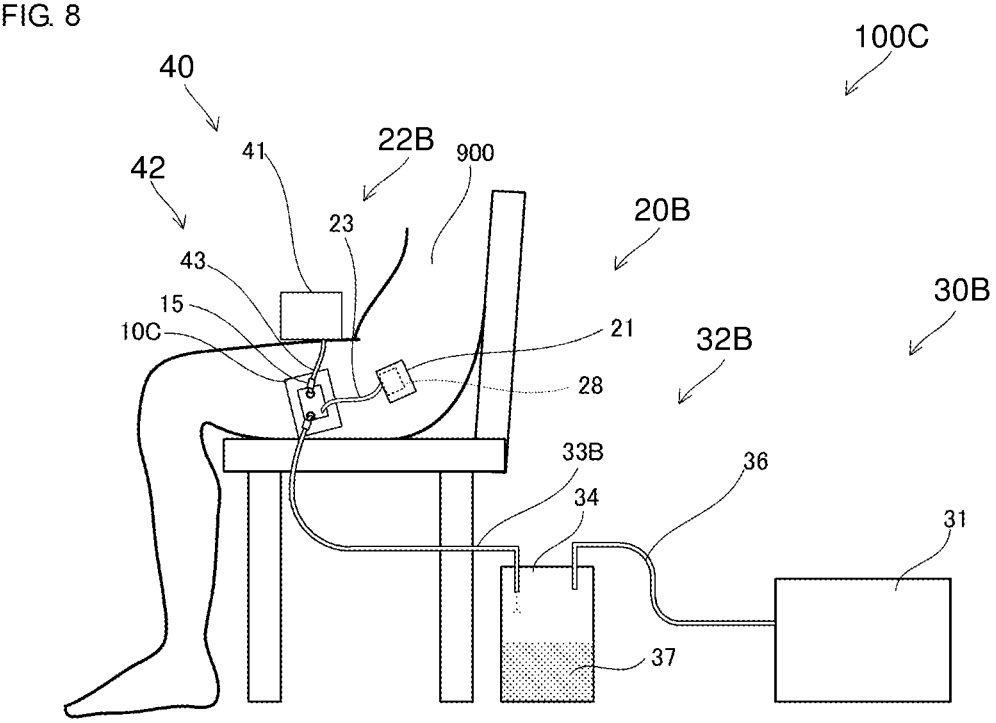
FIG. 8 is an illustration for describing atypical use of the therapy apparatus according to the third embodiment.

As illustrated in FIG. 8, the cleaning tool 40 includes the cleaning solution tank 41 and a conduit 42. The conduit 42 extends from the cleaning solution tank 41 to the closed space 904. A part of the conduit 42 is formed from a rubber tube 43. The rubber tube 43 has a first end attached to the cleaning solution tank 41 and a second end attached to the central portion 12 in the film 11. Specifically, the second end of the rubber tube 43 is fit in the joint tube 15 in the mounting port 44, as illustrated in FIG. 7. Because the second end of the rubber tube 43 can be freely inserted in and removed from the joint tube 15 in the mounting port 44, the cleaning tool 40 can be freely attached to and detached from the wound dressing 10C.

The user 900 detaches the pump device 30B from the wound dressing 10C, attaches the cleaning tool 40 to the wound dressing 10C, and uses the therapy apparatus 100C in a typical manner. When the pump device 20B is driven, the cleaning solution in the cleaning solution tank 41 flows into the closed space 904 through the conduit 42. The surface in the wound region 903 is cleaned with the cleaning solution flowing to the closed space 904. After that, the cleaning solution is transported to the canister 28 through a part of the conduit 22B. The canister 28 stores the cleaning solution after use in cleaning the wound region 903.

The user 900 attaches the cleaning tool 40 and the pump device 30B to the wound dressing 10C and uses the therapy apparatus 100C in an atypical manner. When the pump device 30B is driven, the cleaning solution in the cleaning solution tank 41 flows into the closed space 904 through the conduit 42. The surface in the wound region 903 is cleaned with the cleaning solution flowing to the closed space 904. After that, the cleaning solution is transported to the canister 34 through the rubber tube 33B in the conduit 32B. The canister 34 stores a cleaning solution 37 after use in cleaning the wound region 903.

The therapy apparatus 100C according to the present embodiment can cause negative pressure in the closed space 904 with a sufficient suction flow rate as needed. In addition, when it is necessary to clean the wound region 903 with a large quantity of cleaning solution, because the pump device 30B having a high suction flow rate, is attached to the wound dressing 10C, even if the suction flow rate of the pump device 20B is low, the therapy apparatus 100C can clean the wound region 903 with the cleaning solution in large quantity by sending the cleaning solution to the wound region 903 with a sufficient flow rate as needed.

When the amount of the cleaning solution after use in cleaning is large, because the pump device 30B including the canister 34 having a large storage capacity is attached to the wound dressing 10C, the therapy apparatus 100C can store a larger quantity of cleaning solution after use in cleaning as needed.

If the pump device 30B and pump device 20B are simultaneously driven, the suction flow rate of the pump device 30B may be equal to that of the pump device 20B or may be lower than that of the pump device 20B.

10, 10B, 10C wound dressing
11 film
12 central portion
13, 13C mounting port
14 check valve
15 joint tube
16 filter
17 absorbing member
18 gauze
19 covering member
20, 20A, 20B pump device
21 main body portion
22, 22B conduit
23 rubber tube
25 piezoelectric pump
26 pressure sensor
27 controller
28 canister
30, 30B pump device
31 main body portion
32, 32A, 32B conduit
33, 33A, 33B rubber tube
34 canister
35 exudate 36 rubber tube
37 cleaning solution
40 cleaning tool
41 cleaning solution tank
42 conduit
43 rubber tube
44 mounting port
100, 100A, 100B, 100C, therapy apparatus

The invention claimed is:

1. A negative-pressure wound therapy apparatus comprising:
- a wound dressing adapted for providing a closed space between a central portion of a principal surface of the wound dressing and a wound region by closely contacting a peripheral portion of the principal surface with a periphery of a skin surface in the wound region;
- a first pump device including a first conduit attached to the wound dressing and a first inlet communicating with the closed space through the first conduit; and
- a second pump device including a second conduit freely attachable to and detachable from the wound dressing and a second inlet communicating with the closed space through the second conduit,
- wherein a suction flow rate of the second pump device is higher than a suction flow rate of the first pump device when the first pump device and the second pump device are driven simultaneously,
- the first pump device sucks fluid from the closed space through the first conduit and the first inlet, and
- when the second conduit is attached to the wound dressing the second conduit communicates directly with the closed space, the second pump device sucks fluid from the closed space through the second conduit and the second inlet.

2. The negative-pressure wound therapy apparatus according to claim 1, wherein when the second conduit is attached to the wound dressing, the first pump device and the second pump device are driven simultaneously.

3. The negative-pressure wound therapy apparatus according to claim 1, wherein the first pump device includes a first storage portion disposed in the first conduit,
- the second pump device includes a second storage portion disposed in the second conduit, and
- a storage capacity of the second storage portion is larger than a storage capacity of the first storage portion.

4. The negative-pressure wound therapy apparatus according to claim 3, further comprising a cleaning tool including a third conduit attached to the wound dressing and a third storage portion, the third storage portion communicating with the closed space through the third conduit and configured to store a cleaning solution for cleaning the wound region.

5. The negative-pressure wound therapy apparatus according to claim 1, wherein the first pump device includes a pump drivable by a piezoelectric element.

6. The negative-pressure wound therapy apparatus according to claim 2, wherein the first pump device includes a first storage portion disposed in the first conduit,
- the second pump device includes a second storage portion disposed in the second conduit, and
- a storage capacity of the second storage portion is larger than a storage capacity of the first storage portion.

7. The negative-pressure wound therapy apparatus according to claim 2, wherein the first pump device includes a pump drivable by a piezoelectric element.

8. The negative-pressure wound therapy apparatus according to claim 3, wherein the first pump device includes a pump drivable by a piezoelectric element.

9. The negative-pressure wound therapy apparatus according to claim 4, wherein the first pump device includes a pump drivable by a piezoelectric element.

10. The negative-pressure wound therapy apparatus according to claim 1, wherein the first conduit is disposed on a first end portion side as seen from a central portion in the wound dressing, and the second conduit is disposed on a second end portion side in a direction opposite the first end portion side as seen from the central portion in the wound dressing.

11. The negative-pressure wound therapy apparatus according to claim 4, wherein a location where the third conduit is attached to the wound dressing is nearer to the first conduit than the second conduit, the third conduit is disposed on a first end portion side as seen from the central portion in the wound dressing, and the second conduit is disposed on a second end portion side in a direction opposite to the first end portion as seen from the central portion in the wound dressing.

12. The negative-pressure wound therapy apparatus according to claim 2, wherein the first conduit is disposed on a first end portion side as seen from a central portion in the wound dressing, and the second conduit is disposed on a second end portion side in a direction opposite the first end portion side as seen from the central portion in the wound dressing.

13. A negative-pressure wound therapy apparatus comprising:
- a wound dressing adapted for providing a closed space between a central portion of a principal surface of the wound dressing and a wound region by closely contacting a peripheral portion of the principal surface with a periphery of a skin surface in the wound region;
- a first pump device including a first conduit attached to the wound dressing and a first inlet communicating with the closed space through the first conduit; and
- a second pump device including a second conduit freely attachable to and detachable from the wound dressing and a second inlet communicating with the closed space through the second conduit, the second pump device being isolated from the first pump device,
- wherein a suction flow rate of the second pump device is higher than a suction flow rate of the first pump device when the first pump device and the second pump device are driven simultaneously,
- the first pump device sucks fluid from the closed space through the first conduit and the first inlet, and
- when the second conduit is attached to the wound dressing the second conduit communicates directly with the closed space, the second pump device sucks fluid from the closed space through the second conduit and the second inlet.

* * * * *